US010722216B2

(12) United States Patent
Ito et al.

(10) Patent No.: US 10,722,216 B2
(45) Date of Patent: Jul. 28, 2020

(54) ULTRASOUND IMAGE DIAGNOSTIC APPARATUS

(71) Applicant: Konica Minolta, Inc., Tokyo (JP)

(72) Inventors: Yoshihiko Ito, Yamato (JP); Kazuya Takagi, Machida (JP); Masashi Kunita, Yokohama (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 15/119,609

(22) PCT Filed: Mar. 17, 2016

(86) PCT No.: PCT/JP2016/058534
§ 371 (c)(1),
(2) Date: Aug. 17, 2016

(87) PCT Pub. No.: WO2017/029830
PCT Pub. Date: Feb. 23, 2017

(65) Prior Publication Data
US 2017/0172547 A1    Jun. 22, 2017

(30) Foreign Application Priority Data
Aug. 20, 2015 (JP) ................................ 2015-162394

(51) Int. Cl.
*A61B 8/08* (2006.01)
*A61B 8/00* (2006.01)

(52) U.S. Cl.
CPC .............. *A61B 8/52* (2013.01); *A61B 8/0841* (2013.01); *A61B 8/5207* (2013.01);
(Continued)

(58) Field of Classification Search
None
See application file for complete search history.

(56) References Cited

U.S. PATENT DOCUMENTS

| 5,456,255 A * | 10/1995 | Abe ...................... A61B 8/463 |
| | | 600/441 |
| 2004/0002653 A1 * | 1/2004 | Greppi .................... A61B 8/06 |
| | | 600/439 |

(Continued)

FOREIGN PATENT DOCUMENTS

| CN | 101623204 A | 1/2010 |
| EP | 1281368 A2 | 2/2003 |

(Continued)

OTHER PUBLICATIONS

Frank, "Denoising of continuious-wave time-of-flight depth images using confidence measures". Optical Engineering, 2008. vol. 48, No. 7, pp. 1-24.*

(Continued)

*Primary Examiner* — Katherine L Fernandez
*Assistant Examiner* — Yi-Shan Yang
(74) *Attorney, Agent, or Firm* — Lucas & Mercanti, LLP

(57) ABSTRACT

An ultrasound image diagnostic apparatus includes, a transmitter to repeat alternating supply of first pulse signals and second pulse signals to the ultrasound probe, the second pulse signals being generated by polarity inversion of the first pulse signals; a receiver; a memory to store first sound ray data corresponding to the first pulse signals; an adder to add the stored first sound ray data and second sound ray data corresponding to the second pulse signals; a line-signal processor to generate fundamental line data and harmonic line data; a needle emphasizing signal processor to generate needle image data from the generated fundamental image data; a harmonic signal processor to generate harmonic image data; a synthesizer to combine the needle image data and the harmonic image data; and a display controller to display the synthesized image data.

13 Claims, 7 Drawing Sheets

(52) U.S. Cl.
CPC .......... *A61B 8/5223* (2013.01); *A61B 8/5246* (2013.01); *A61B 8/5269* (2013.01); *A61B 8/56* (2013.01)

(56) References Cited

U.S. PATENT DOCUMENTS

| | | | | |
|---|---|---|---|---|
| 2006/0241451 | A1* | 10/2006 | Nakaya | A61B 8/0833 600/443 |
| 2010/0312117 | A1* | 12/2010 | Fernandez | A61B 8/0833 600/458 |
| 2011/0077517 | A1* | 3/2011 | Satou | A61B 8/00 600/443 |
| 2013/0165788 | A1* | 6/2013 | Osumi | A61B 8/4444 600/443 |
| 2015/0094569 | A1* | 4/2015 | Ohuchi | A61B 8/0841 600/424 |
| 2015/0245819 | A1* | 9/2015 | Yoshiara | A61B 8/06 600/424 |
| 2015/0374343 | A1* | 12/2015 | Shan | A61B 8/0858 600/443 |
| 2017/0071475 | A1* | 3/2017 | Irisawa | A61B 8/13 |
| 2018/0000452 | A1* | 1/2018 | Adams | G01S 7/52095 |

FOREIGN PATENT DOCUMENTS

| | | |
|---|---|---|
| JP | 2006150069 A | 10/2005 |
| JP | 2012096095 A | 5/2012 |
| JP | 2014028128 A | 2/2014 |
| JP | 2014100556 A | 6/2014 |
| WO | 2011/154782 A1 | 12/2011 |

OTHER PUBLICATIONS

International Search Report dated Aug. 20, 2015 for PCT/JP2016/058534.
Written Opinion dated Apr. 26, 2016 for PCT/JP2016/058534 and partial English translation.
Extended European Search Report dated Jun. 14, 2018 from European Application No. 16836822.3.
CNIPA, Office Action for the related Chinese Application No. 201680048217.7, dated Feb. 3, 2020, with English translation.

* cited by examiner

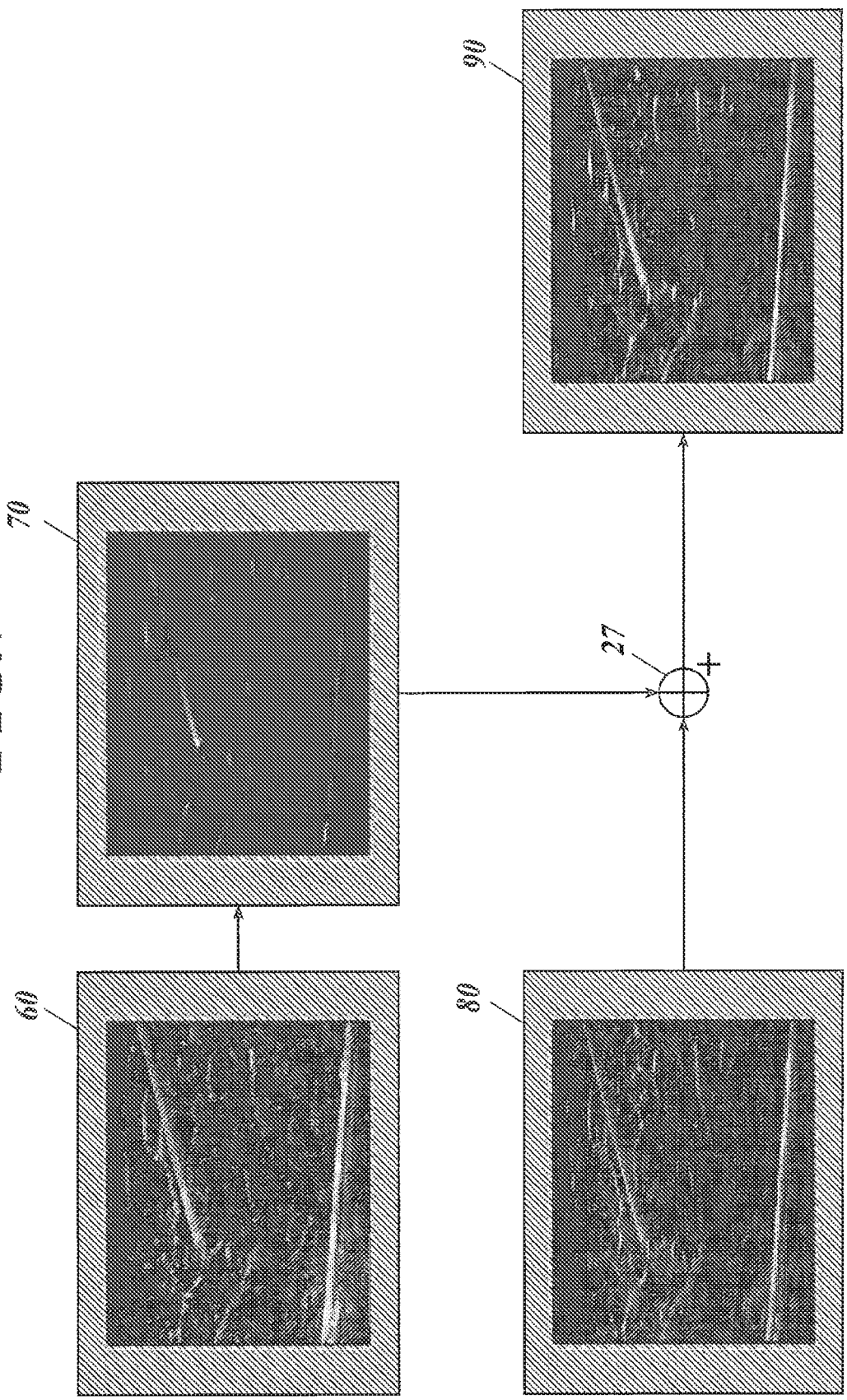

ULTRASOUND IMAGE DIAGNOSTIC APPARATUS

CROSS REFERENCE TO RELATED APPLICATION

This Application is a 371 of PCT/JP2016/058534 filed on Mar. 17, 2016, which, in turn, claimed the priority of Japanese Patent Application No. JP 2015-162394 filed on Aug. 20, 2015, both applications are incorporated herein by reference.

TECHNICAL FIELD

The present invention relates to an ultrasound image diagnostic apparatus.

BACKGROUND ART

Traditional ultrasound image diagnostic apparatuses inspect the interiors of subjects through emitting ultrasound waves into the subjects to receive ultrasound waves (echoes) reflected from the subjects, and conducting predetermined processes to signal data on the received echoes. Such ultrasound image diagnostic apparatuses are used for various purposes, such as medical tests and treatments and inspection of the internal structures of buildings.

The ultrasound image diagnostic apparatuses can generate images having good contrast from the harmonic components (e.g., frequencies 2f0 and 3f0) of transmitting signals relative to their fundamental components (frequency f0). This technique is called tissue harmonic imaging (THI).

These harmonic components are mainly caused by the non-linear distortion of ultrasound waves during propagation in a subject. In specific, incident ultrasound waves in a living body are distorted by the non-linear response of tissues during propagation in the tissues, resulting in increased harmonic components. The response signals corresponding to the ultrasound waves thus include, for example, components of frequencies 2f0 and 3f0 (two and three times the frequency f0 of fundamental waves).

The harmonic components in the tissue harmonic imaging can be extracted by a known method, such as a filtering technique or pulse inversion technique.

In the filtering technique, a band-pass filter having a center frequency of 2f0, for example, extracts 2f0 harmonic components from response signals. In the pulse inversion technique, the apparatuses transmit first and second pulse signals that are polarity-inverted or time-inverted at a predetermined time interval, and combine their response signals to offset the fundamental components, thereby emphasizing the second harmonic components.

A typical ultrasound image diagnostic apparatus based on the pulse inversion technique generates fundamental image signals from first echoes after the first transception (transmission and reception) of fundamental ultrasound waves, generates harmonic image signals through addition of second echoes after the second transception of inverted fundamental ultrasound waves to the first echoes, and then combines the fundamental image signals with the harmonic image signals, which are weighted depending on the depth for each line (scanning line) (refer to Patent Literature 1). The synthesized image is made of a harmonic image in a shallow portion and a fundamental image in a deep portion, and has few artifacts and sufficient sensitivity even in the deep portion.

The use of the ultrasound image diagnostic apparatuses is not limited to ultrasound image display of a subject based on the processed data on received echoes. The ultrasound image diagnostic apparatuses are also used to identify and visualize the position of a puncture needle relative to a specific portion (target) in a subject during the inserting of the puncture needle into the target for sampling the target, discharging water from the target, or injecting or indwelling an agent or marker into the target. Such ultrasound image can achieve rapid, certain, and ready treatment for the target in the subject.

The pulse inversion technique can be applied to the imaging of a subject using such a puncture needle. For example, a typical ultrasound image diagnostic apparatus repeats the first transception of positive ultrasound waves, the second transception of negative ultrasound waves (inverted from the positive ultrasound waves), and the third transception of negative ultrasound waves; generates a normal mode image through combining the first echoes and the second echoes; and generates a puncture mode image through combining the first echoes and the third echoes (refer to Patent Literature 2). The normal mode image is based on a relatively low pulse repetition frequency (PRF) and thus has reduced motion artifacts caused by motions of the living body, whereas the puncture mode image is based on a relatively high PRF and can thus capture motion artifacts caused by motions of the puncture needle well.

PRIOR ART DOCUMENT

Patent Literature

[Patent Literature 1] Japanese Unexamined Patent Application Publication No. 2012-96095
[Patent Literature 2] Japanese Unexamined Patent Application Publication No. 2006-150069

SUMMARY OF INVENTION

Problems to be Solved by the Invention

Unfortunately, the ultrasound image diagnostic apparatus disclosed in Patent Literature 2 requires three cycles of transception (transmission and reception) of ultrasound waves to obtain a normal mode image and a puncture mode image. The obtained images thus have lower frame rates compared to those based on two cycles of transception.

Furthermore, the ultrasound image diagnostic apparatus disclosed in Patent Literature 2 generates a puncture mode image from harmonic components extracted by the pulse inversion technique. The harmonic components form an ultrasound beam that is narrow not only in the long axis direction but also in the short axis direction (direction of slicing), and thus are advantageous in a brightness (B) mode image (normal mode image). Unfortunately, in a puncture mode image, such a narrow ultrasound beam often misses the puncture needle moving away from the plane of slicing and cannot readily capture the puncture needle.

In addition, the ultrasound image diagnostic apparatus disclosed in Patent Literature 2 emphasizes tissues around the puncture needle in addition to motion artifacts caused by motions of the living body in a puncture mode image.

An object of the present invention is to obtain an ultrasound image clearly capturing a puncture needle and having high spatial resolution. Another object is to prevent reduction of frame rate.

Means for Solving the Problem

In view of the above problems, according to an aspect of the present invention, there is provided an ultrasound image diagnostic apparatus for capturing an image of a subject into which a puncture needle is inserted, the apparatus including:

an ultrasound probe to transmit ultrasound waves to the subject in response to received pulse signals and output response signals in response to received echoes from the subject;

a transmitter to repeat alternating supply of first pulse signals and second pulse signals to the ultrasound probe, the second pulse signals being generated by polarity inversion of the first pulse signals;

a receiver to receive the response signals from the ultrasound probe and generate sound ray data;

a memory to store first sound ray data corresponding to the first pulse signals;

an adder to generate harmonic sound ray data through addition of the stored first sound ray data and second sound ray data corresponding to the second pulse signals;

a line-signal processor to generate fundamental line data from the generated first sound ray data and generate harmonic line data from the generated harmonic sound ray data;

a fundamental image generator to generate fundamental image data from the generated fundamental line data;

a needle image generator to generate needle image data from the generated fundamental image data, the needle image data including an emphasized needle area corresponding to the puncture needle;

a harmonic image generator to generate harmonic image data from the generated harmonic line data;

a synthesizer to generate synthesized image data through combining the generated needle image data and the generated harmonic image data; and a display controller to control a display to display the generated synthesized image data.

A second aspect of the ultrasound image diagnostic apparatus according to aspect 1, further including a switch to output one of the harmonic sound ray data and the generated first sound ray data, the harmonic sound ray data being generated through addition of the stored first sound ray data and the second sound ray data corresponding to the second pulse signals.

A third aspect of the ultrasound image diagnostic apparatus according to aspect 1 or 2, wherein the line-signal processor generates the fundamental line data through a process for fundamental images on the generated first sound ray data, and generates the harmonic line data through a process for harmonic images on the generated harmonic sound ray data.

A fourth aspect of the ultrasound image diagnostic apparatus according to any one of aspects 1 to 3, wherein the needle image generator includes:

a first smoothing processor to generate first smoothed image data through smoothing of the generated fundamental image data;

a second smoothing processor to generate second smoothed image data through smoothing of the fundamental image data with higher intensity than the intensity of the smoothing for the first smoothed image data; and a subtracter to calculate differences of the second smoothed image data from the first smoothed image data.

A fifth aspect of the ultrasound image diagnostic apparatus according to aspect 4, wherein the second smoothing processor performs smoothing with higher intensity in a horizontal direction than in a vertical direction on the fundamental image data in the actual dimensions.

A sixth aspect of the ultrasound image diagnostic apparatus according to aspect 4, wherein the needle image generator determines a first smoothing region for generation of the first smoothed image data and a second smoothing region for generation of the second smoothed image data, the first smoothing region being disposed in the substantial center of the second smoothing region, the first smoothing region including a smoothing target pixel in the substantial center.

A seventh aspect of the ultrasound image diagnostic apparatus according to aspect 6, wherein the first smoothing region is disposed in the substantial center of the second smoothing region in the horizontal or vertical direction of the fundamental image data.

An eighth aspect of the ultrasound image diagnostic apparatus according to aspect 6 or 7, further including a first input unit to receive input of a display depth, wherein the first smoothing processor generates the first smoothed image data with a smaller first smoothing region as the display depth increases, and the second smoothing processor generates the second smoothed image data with a smaller second smoothing region as the display depth increases.

A ninth aspect of the ultrasound image diagnostic apparatus according to any one of aspects 1 to 8, further comprising a first contrast corrector to perform first contrast correction involving gradation correction to the generated needle image data.

A tenth aspect of the ultrasound image diagnostic apparatus according to any one of aspects 1 to 9, further including a second contrast corrector to perform second contrast correction involving gradation correction to the generated harmonic image data.

An eleventh aspect of the ultrasound image diagnostic apparatus according to any one of aspects 1 to 10, further including:

a second input unit to receive input of a synthesizing factor for the needle image data; and a multiplier to multiply brightness values of the generated needle image data by the input synthesizing factor, wherein the synthesizer generates the synthesized image data through combining the needle image data multiplied by the synthesizing factor and the generated harmonic image data.

Advantageous Effect of Invention

The invention can obtain an ultrasound image clearly capturing a puncture needle and having high spatial resolution. The invention can also prevent reduction of frame rate.

BRIEF DESCRIPTION OF DRAWINGS

FIG. 7 illustrates example composition of ultrasound images; and

EMBODIMENT FOR CARRYING OUT THE INVENTION

Embodiments of the invention will now be described in detail with reference to the accompanying drawings. The illustrated examples should not be construed to limit the invention.

Figure 1:
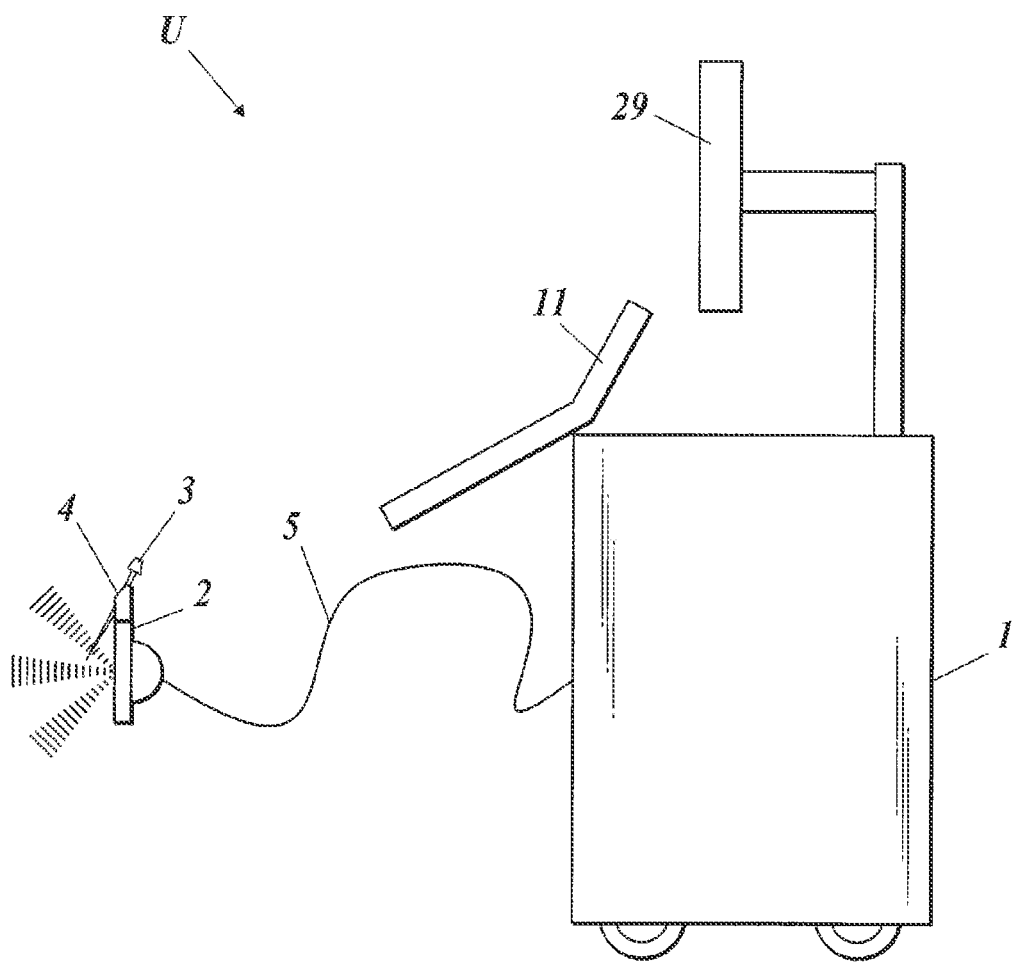
FIG. 1 illustrates the appearance of an ultrasound image diagnostic apparatus.
Figure 2:
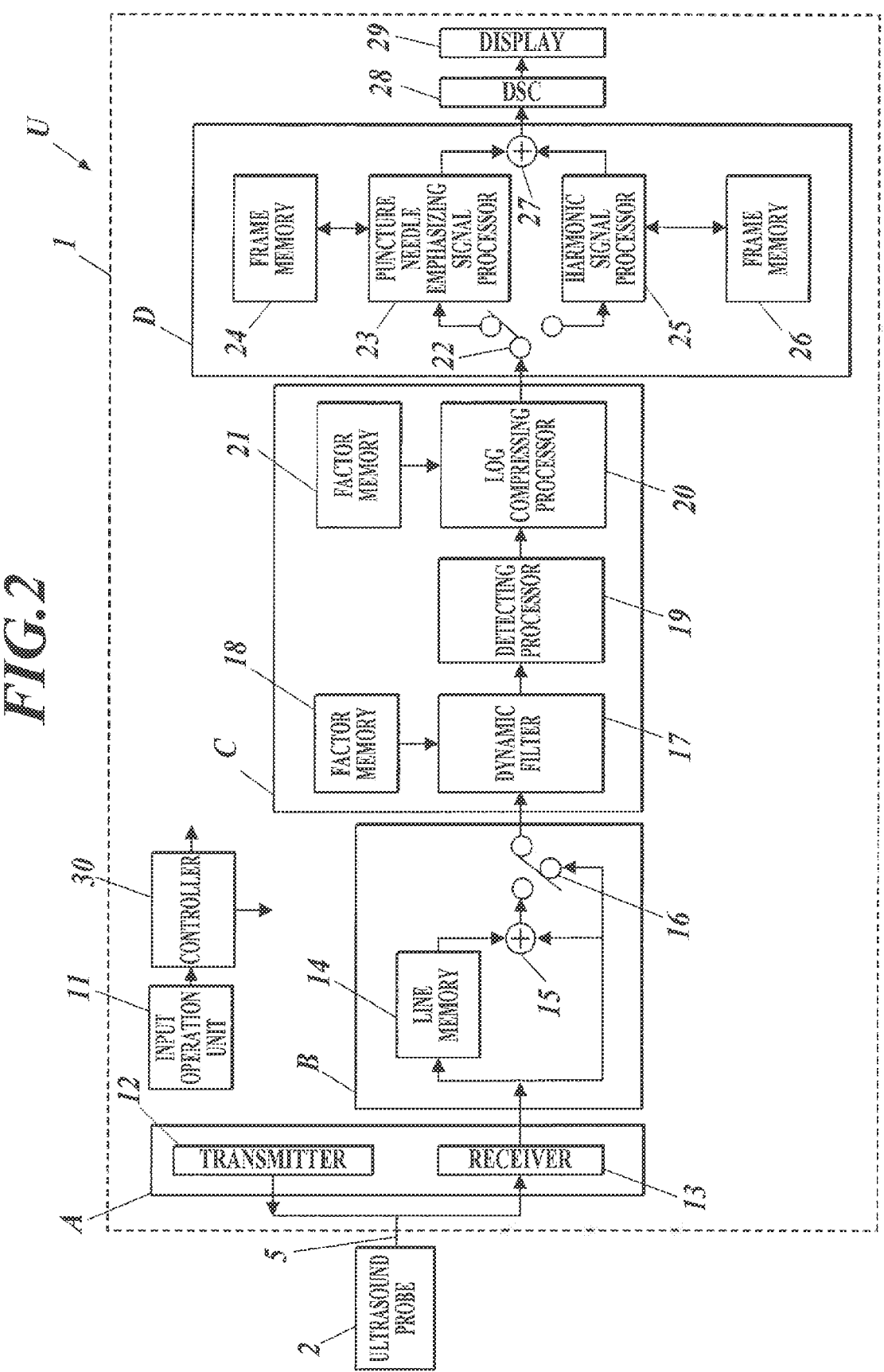
FIG. 2 is a block diagram illustrating the schematic configuration of an ultrasound image diagnostic apparatus.
Figure 3:
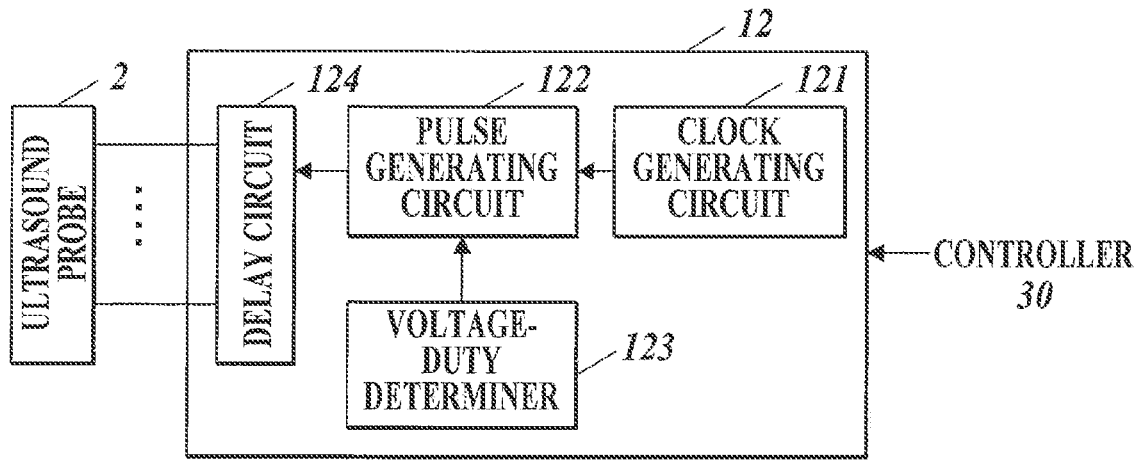
FIG. 3 is a block diagram illustrating the functional configuration of a transmitter.
Figure 4:
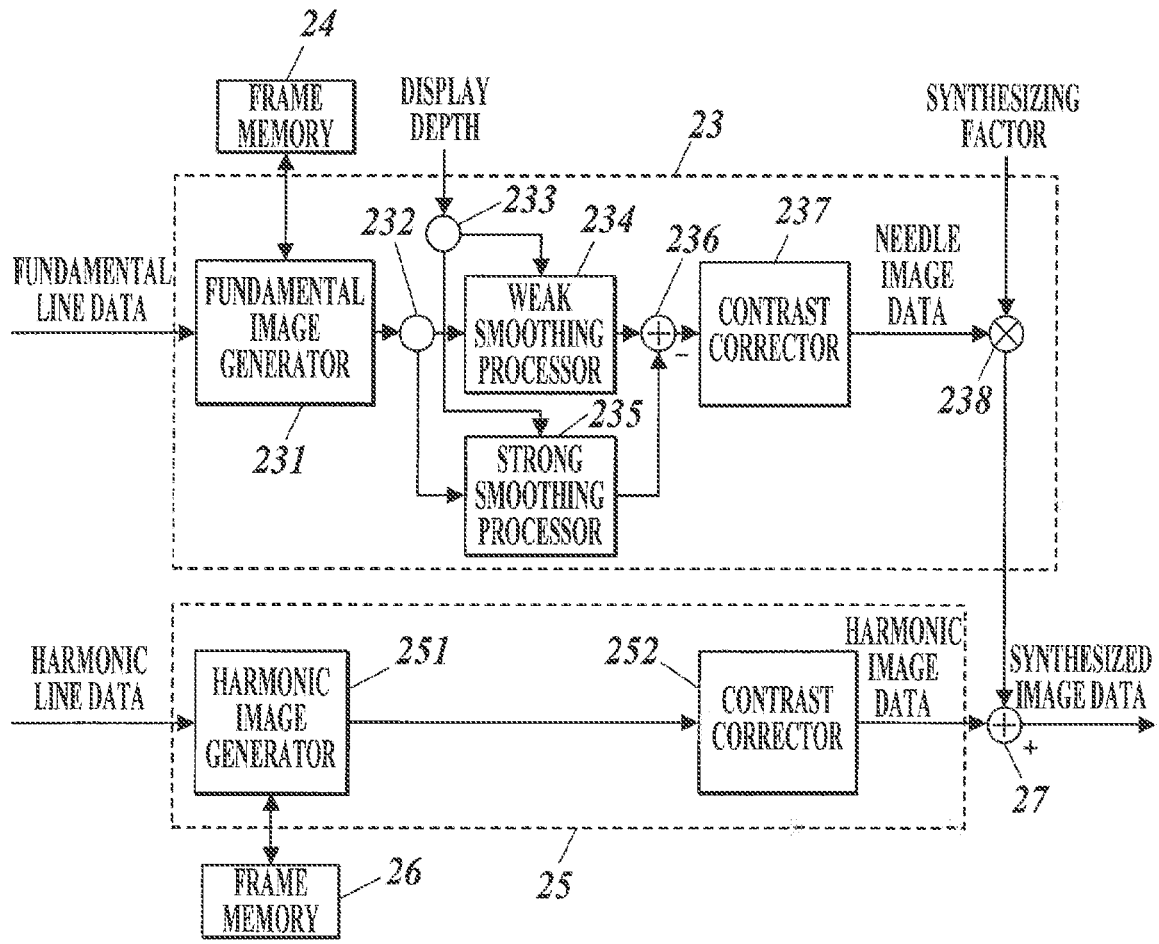
FIG. 4 is a block diagram illustrating the functional configurations of a puncture needle emphasizing signal processor according to a first embodiment and a harmonic signal processor.

The configuration of an apparatus according to the present embodiment will now be described with reference to FIGS. 1 to 6C. FIG. 1 illustrates the whole appearance of an ultrasound image diagnostic apparatus U according to the embodiment. FIG. 2 is a block diagram illustrating the functional configuration of the ultrasound image diagnostic apparatus U. FIG. 3 is a block diagram illustrating the functional configuration of a transmitter 12. FIG. 4 is a block diagram illustrating the functional configurations of a puncture needle emphasizing signal processor 23 and a harmonic signal processor 25.

With reference to FIG. 1, the ultrasound image diagnostic apparatus U according to the present embodiment includes an ultrasound image diagnostic apparatus main unit 1, an ultrasound probe 2 connected to the ultrasound image diagnostic apparatus main unit 1 with a cable 5 or by wireless communication means, a puncture needle 3, and an attachment 4 mounted to the ultrasound probe 2.

The ultrasound probe 2 transmits ultrasound waves (transmitting ultrasound waves) to a subject (not shown), such as a living body, and receives the ultrasound waves (echoes) reflected from the subject. The ultrasound image diagnostic apparatus main unit 1 supplies the ultrasound probe 2 with electrical driving signals to cause the ultrasound probe 2 to transmit ultrasound waves to the subject, and generates an ultrasound image of the interior of the subject on the basis of electrical response signals, which are generated by the ultrasound probe 2 in response to reception of the echoes from the subject.

The ultrasound probe 2 includes a stack of, for example, a backing layer, a piezoelectric layer, an acoustic matching layer, and an acoustic lens. The piezoelectric layer is equipped with oscillators (not shown) having piezoelectric elements. The oscillators are disposed, for example, in a one-dimensional array along the orientation direction. According to the embodiment, the ultrasound probe 2 includes 192 oscillators, for example. Alternatively, the oscillators may be disposed in a two-dimensional array. The number of the oscillators may be appropriately varied. Although the ultrasound probe 2 is an electronic scanning probe of a linear scanning type in the embodiment, the ultrasound probe 2 may be a mechanical or electronic scanning probe of a linear scanning, sector scanning, or convex scanning type.

The puncture needle 3 is elongated and hollow, and is configured to be inserted into a subject at an angle defined by the attachment 4. The puncture needle 3 may be replaced with one having any appropriate thickness, length, and tip shape depending on a target (specimen) to be sampled or the type and volume of an agent to be injected.

The attachment 4 retains the puncture needle 3 in the determined orientation (direction). The attachment 4 is mounted to a side of the ultrasound probe 2 and can appropriately change the orientation of the puncture needle 3 depending on a desired angle of the puncture needle 3 relative to the subject. The attachment 4 can shift the puncture needle 3 in the puncture direction and also insert the puncture needle 3 while rotating (spinning) the puncture needle 3 about its central axis. Alternatively, the ultrasound probe 2 may be directly provided with a guide for retaining the puncture needle 3 in the puncture direction, in place of the attachment 4.

With reference to FIG. 2, the ultrasound image diagnostic apparatus main unit 1 includes an input operation unit 11 (functioning as a first input unit or a second input unit), a display 29, a transceiver A, a line adding unit B, a line-signal processor C, a frame-signal processor D, a digital scan converter (DSC) 28 (functioning as a display controller), and a controller 30.

The transceiver A includes a transmitter 12 and a receiver 13. The line adding unit B is provided with a line memory 14 (functioning as a memory), an adder 15, and a switch 16. The line-signal processor C includes a dynamic filter 17, a factor memory 18, a detecting processor 19, a log compressing processor 20, and a factor memory 21. The frame-signal processor D is provided with a switch 22, a puncture needle emphasizing signal processor 23, frame memories 24 and 26, a harmonic signal processor 25, and a synthesizer 27.

The input operation unit 11 includes a push button switch, a keyboard, a mouse, a trackball, or any combination thereof. The input operation unit 11 converts an operational input by a user (an inspector, such as a technician or doctor) into operation signals and inputs the signals to the ultrasound image diagnostic apparatus main unit 1. In specific, the input operation unit 11 receives input of a display depth (i.e., the depth of a target site from the surface of the subject) and a synthesizing factor (i.e., a factor for needle image data on the puncture needle 3 in the synthesis of the needle image data and harmonic image data).

The transmitter 12 is a circuit that supplies the ultrasound probe 2 with electrical driving signals via the cable 5 to cause the ultrasound probe 2 to generate transmitting ultrasound waves, under the control of the controller 30. In specific, the transmitter 12 repeats alternating output of pulse driving signals corresponding to positive fundamental waves for a single line of an ultrasound image and pulse driving signals corresponding to negative fundamental waves (generated by polarity inversion of the positive fundamental waves) for the same line, on the basis of the pulse inversion technique of THI. The transmitter 12 thus outputs pulse signals corresponding to positive and negative fundamental waves for multiple lines.

With reference to FIG. 3, the transmitter 12 includes, for example, a clock generating circuit 121, a pulse generating circuit 122, a voltage-duty determiner 123, and a delay circuit 124.

The clock generating circuit 121 generates clock signals for determining the transmission timing and frequency of driving signals. The pulse generating circuit 122 generates pulse signals (driving signals) in predetermined cycles. The pulse generating circuit 122 can generate rectangular pulse signals, for example, through switching their voltage among determined five values (+HV/+MV/0/−MV/−HV) and determining the duty ratio. Although the pulse signals corresponding to the positive and negative fundamental waves have the same amplitude in the embodiment, this feature should not be construed to limit the invention. Although the voltage of the pulse signals is switched among five values in the embodiment, the number of the values may be any appropriate number (preferably five or smaller), and the number is not limited to five. This configuration can improve the flexibility of control over frequency components at low costs and can enhance the resolution of transmitting ultrasound waves.

The voltage-duty determiner 123 determines the voltage and duty ratio of pulse signals to be output from the pulse generating circuit 122. In other words, the pulse generating circuit 122 outputs pulse signals shaped in accordance with the voltage and duty ratio determined by the voltage-duty determiner 123. The voltage and duty ratio may be changed by, for example, input from the input operation unit 11.

Referring back to FIG. 2, the receiver 13 is a circuit that receives electrical response signals from the ultrasound probe 2 via the cable 5 or wireless communication means, under the control of the controller 30. The receiver 13 includes, for example, an amplifier, an analog-digital conversion circuit, and a phasing adding circuit. The amplifier is a circuit that amplifies the response signals by a predetermined gain for the respective paths from the oscillators. The analog-digital conversion circuit performs analog-digital conversion (A/D conversion) to the amplified signals. The phasing adding circuit phases the digitized signals by adding the delay times for the respective paths from the oscillators to the signals, and then adds up the phased signals to generate sound ray data.

The line adding unit B is equipped with the line memory 14, the adder 15, and the switch 16.

The line memory 14 stores sound ray data on the pulse signals corresponding to positive fundamental waves for a single line from the receiver 13. The adder 15 reads the sound ray data from the line memory 14, and adds the read sound ray data to sound ray data on the pulse signals corresponding to negative fundamental waves for the same line from the receiver 13 (i.e., sound ray data on the pulse signals corresponding to negative fundamental waves output from the transmitter 12 subsequently to the pulse signals corresponding to positive fundamental waves indicated by the read sound ray data), under the control of the controller 30. This addition by the adder 15 offsets the positive and negative fundamental components, allowing extraction of sound ray data on harmonic components synthesized mainly of second harmonic waves.

The switch 16 varies the path of sound ray data output to the line-signal processor C (dynamic filter 17) for each line, under the control of the controller 30. In specific, in response to input of the sound ray data on the pulse signals corresponding to positive fundamental waves for a single line to the line adding unit B, the switch 16 connects the path to the receiver 13 so that the input sound ray data is directly output; whereas in response to input of the sound ray data on the pulse signals corresponding to negative fundamental waves for the same line to the line adding unit B, the switch 16 connects the path to the adder 15 so that the sound ray data on harmonic components generated by the adder 15 is output.

The line adding unit B thus requires only two cycles of transception of ultrasound waves to output sound ray data on fundamental and harmonic components, achieving a higher frame rate than that of a traditional apparatus requiring three cycles.

The dynamic filter 17 is a digital filter for filtering the sound ray data output from the line adding unit B (switch 16) under the control of the controller 30. The dynamic filter 17 has multiple taps, and the filtering characteristics can be varied through adjustment of the factors for the taps. The factor memory 18 stores the tap factor for fundamental images (needle images for detecting the puncture needle 3) and the tap factor for harmonic images.

In response to input of the sound ray data on the pulse signals corresponding to positive fundamental waves for a single line from the line adding unit B, the dynamic filter 17 reads the tap factor for fundamental images from the factor memory 18 and applies the factor to the taps, to filter and transmit the fundamental components of the input sound ray data. In response to input of the sound ray data on the harmonic components for the same line from the line adding unit B, the dynamic filter 17 reads the factor for harmonic images from the factor memory 18 and applies the tap factor to the taps, to filter and transmit the second harmonic components of the input sound ray data.

The detecting processor 19 extracts envelope data through envelope detection of the sound ray data from the dynamic filter 17, under the control of the controller 30.

The log compressing processor 20 adjusts the gain of the envelope data output from the detecting processor 19 through log compression, and outputs the resulting data as line data indicating brightness values of the image, under the control of the controller 30. The factor memory 21 stores the log-compression factor for fundamental images for narrowing the dynamic range and the log-compression factor for harmonic images for broadening the dynamic range.

In response to input of the envelope data on the pulse signals corresponding to positive fundamental waves for a single line from the detecting processor 19, the log compressing processor 20 reads the log-compression factor for fundamental images from the factor memory 21, narrows the dynamic range of the input envelope data through log compression depending on the read factor, and then outputs the resulting data as fundamental line data. In response to input of the envelope data on the harmonic components for the same line from the detecting processor 19, the log compressing processor 20 reads the log-compression factor for harmonic images from the factor memory 21, broadens the dynamic range of the input envelope data through log compression depending on the read factor, and then outputs the resulting data as harmonic line data.

The switch 22 varies the path of image data from the line-signal processor C (log compressing processor 20) for each line, under the control of the controller 30. In specific, in response to input of the fundamental line data on the pulse signals corresponding to positive fundamental waves for a single line, the switch 22 connects the path to the puncture needle emphasizing signal processor 23 so that it receives the fundamental line data; whereas in response to input of the harmonic line data on the harmonic components for the same line, the switch 22 connects the path to the harmonic signal processor 25 so that it receives the harmonic line data.

The puncture needle emphasizing signal processor 23 infers the background of the input image on the basis of the image data stored in the frame memory 24, and extracts the difference between the background and the input image to emphasize the puncture needle.

The DSC 28 converts synthesized image data, which is received from the frame-signal processor D (synthesizer 27), into image signals for the display 29 through processes, such as coordinate conversion, and outputs the image signals, under the control of the controller 30.

Examples of the display 29 include a liquid crystal display (LCD), a cathode-ray tube (CRT) display, an organic electroluminescent (EL) display, an inorganic EL display, and a plasma display. The display 29 displays an ultrasound image on its screen in accordance with the image signals output from the DSC 28.

The controller 30 includes, for example, a central processing unit (CPU), a read only memory (ROM), and a random access memory (RAM). The controller 30 reads various processing programs, such as a system program, from the ROM and loads the programs in the RAM, to comprehensively control the operations of the individual components of the ultrasound image diagnostic apparatus U under the instructions of the programs. The ROM includes a nonvolatile memory, such as a semiconductor memory. The ROM stores a system program for the ultrasound image diagnostic apparatus U, various processing programs executable under the system program, and various pieces of data. These programs are stored in the form of computer-readable program codes, and the CPU sequentially executes operations under the instructions corresponding to the program codes. The RAM defines a work area for temporarily storing various programs to be executed by the CPU and data related to the programs. FIG. 2 illustrates only some of the control lines from the controller 30 to the individual components.

Hardware circuits, such as integrated circuits, may have some or all of the functions of the individual functional blocks, i.e., the transceiver A, the line adding unit B, the line-signal processor C, the frame-signal processor D, and the DSC 28 of the ultrasound image diagnostic apparatus U. Examples of the integrated circuits include large scale integration (LSI) circuits. The LSI circuit is also referred to as IC, system LSI circuit, super LSI circuit, or ultra LSI circuit depending on its degree of integration. The integration may be achieved by any dedicated circuit, general-purpose processor, field programmable gate array (FPGA), or reconfigurable processor, which has reconfigurable connection and setting of circuit cells in the LSI, other than the LSI. Alternatively, software may have part or all of the functions of the individual functional blocks. In this case, the software is stored in one or more recording media (e.g., ROMs), optical disks, or hard disks, and is executed by a processor.

With reference to FIG. 4, the puncture needle emphasizing signal processor 23 includes a fundamental image generator 231, branches 232 and 233, a weak smoothing processor 234 (functioning as a first smoothing processor), a strong smoothing processor 235 (functioning as a second smoothing processor), a subtracter 236, a contrast corrector 237 (functioning as a first contrast corrector), and a multiplier 238. The harmonic signal processor 25 is provided with a harmonic image generator 251 and a contrast corrector 252 (functioning as a second contrast corrector).

The fundamental image generator 231 sequentially stores pieces of fundamental line data, which is received from the switch 22, into the frame memory 24, under the control of the controller 30. After storing a single frame of fundamental line data, the fundamental image generator 231 reads the single frame of fundamental line data from the frame memory 24 and outputs the single frame of fundamental image data. The frame memory 24 can store at least one frame of fundamental line data.

The branch 232 outputs the fundamental image data received from the fundamental image generator 231 to the weak smoothing processor 234 and the strong smoothing processor 235. The branch 233 outputs the display depth, which is input by the user from the input operation unit 11 via the controller 30, to the weak smoothing processor 234 and the strong smoothing processor 235.

The weak smoothing processor 234 performs smoothing with relatively low intensity to the fundamental image data from the branch 232 depending on the display depth from the branch 233, and then outputs the smoothed data. The strong smoothing processor 235 performs smoothing with relatively high intensity to the fundamental image data from the branch 232 depending on the display depth from the branch 233, and then outputs the smoothed data. The smoothing by the weak smoothing processor 234 is weaker than that by the strong smoothing processor 235. In other words, the smoothing by the strong smoothing processor 235 is stronger than that by the weak smoothing processor 234.

The process of the smoothing will now be explained with reference to FIGS. 5 and 6A to 6C. The smoothing based on averaging is described as an example.

Figure 5:
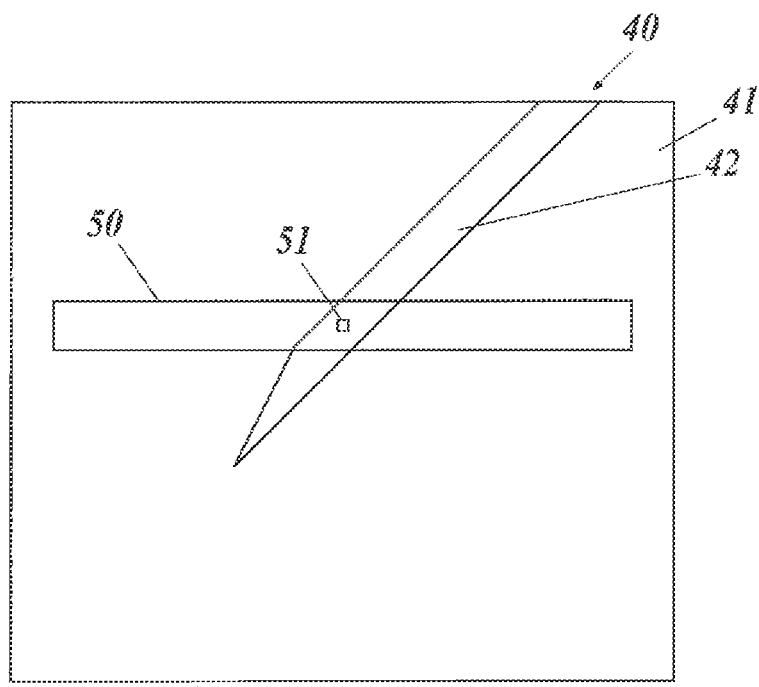
FIG. 5 illustrates a detection area for smoothing in a fundamental image.

FIG. 5 illustrates a positional relationship between a detection area for smoothing and a smoothing target in a fundamental image 40.

The horizontal direction in an ultrasound image corresponds to the direction of the array of the elements (oscillators) in the ultrasound probe 2. FIG. 5 illustrates an ultrasound image, at the top of which the elements of the ultrasound probe 2 are disposed in the right and left direction, and which includes a detection area 50 elongated in the horizontal direction.

The vertical direction corresponds to the direction orthogonal to the array of the elements in the ultrasound probe 2 (i.e., the up and down direction in FIG. 5).

The fundamental image 40 is an ultrasound image (B mode image) based on fundamental image data, and has a subject area 41 representing the subject and a needle area 42 representing the puncture needle 3 inserted in the subject, as illustrated in FIG. 5. The upper side of the subject area 41 (i.e., the top edge of the fundamental image 40) depicts the surface of the subject. The weak smoothing processor 234 and the strong smoothing processor 235 perform smoothing based on the detection area 50 around a smoothing target pixel 51 among all the pixels of the fundamental image 40, to generate the smoothed fundamental image data, under the control of the controller 30.

The smoothing based on averaging is performed in a rectangular area, like the detection area 50 in FIG. 5.

Figure 6A:
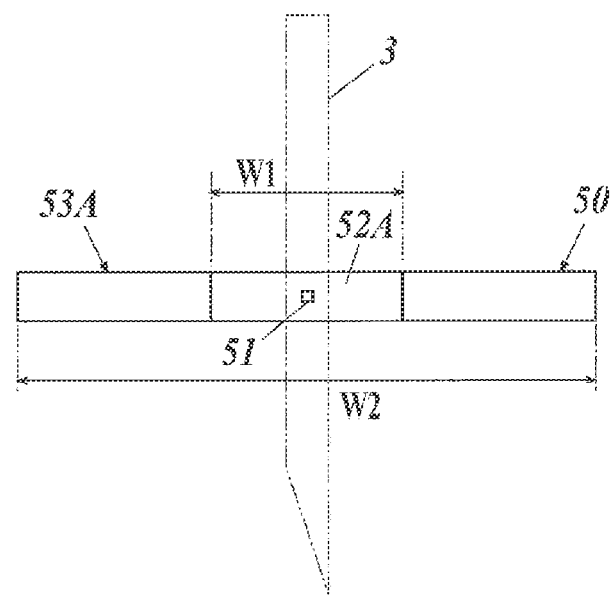
FIG. 6A illustrates a first example of smoothing regions.

With reference to FIG. 6A, the detection area 50 in an image in the actual dimensions is a rectangle having a longer horizontal width than the vertical length, and includes the smoothing target pixel 51 near the center.

The detection area 50 is composed of a relatively weak smoothing region 52A, which has a rectangular shape having a width W1 and is disposed in the substantial center in the horizontal direction of the detection area 50, and a relatively strong smoothing region 53A, which has a rectangular shape having a width W2 and ranges over the entire detection area 50.

In the weak smoothing region 52A and the strong smoothing region 53A, the needle area representing the puncture needle 3 in the fundamental image is emphasized for detection. In the case of a constant resolution regardless of the display depth, the width of the needle area in the fundamental image decreases as the display depth increases. In view of this feature, the sizes of the weak smoothing region 52A and the strong smoothing region 53A are designed to decrease without variations in their shapes as the display depth increases. The same holds true for weak smoothing regions 52B and 52C and strong smoothing regions 53B and 53C (described below).

The weak smoothing processor 234 performs weak smoothing that involves selection of a single smoothing target pixel 51 from the input fundamental image data, and calculation of the average value of the weak smoothing region 52A around the smoothing target pixel 51. The weak smoothing processor 234 repeats the selection of an unselected pixel from the input fundamental image data and the averaging operation, to generate weakly-smoothed fundamental image data.

The strong smoothing processor 235 performs strong smoothing that involves selection of a single smoothing target pixel 51 from the input fundamental image data, and calculation of the average value of the strong smoothing region 53A around the smoothing target pixel 51. The strong smoothing processor 235 repeats the selection of an unselected pixel from the input fundamental image data and the averaging operation, to generate strongly-smoothed fundamental image data.

The weak smoothing by the weak smoothing processor 234 can remove small noises, such as speckles, from the fundamental image. The strong smoothing by the strong smoothing processor 235 can estimate the brightness values of the background of the fundamental image, other than the needle area.

With reference to FIG. 4, the subtracter 236 subtracts the strongly-smoothed fundamental image data received from the strong smoothing processor 235 from the weakly-smoothed fundamental image data received from the weak smoothing processor 234, to generate and output the fundamental image data (needle image data) including the emphasized puncture needle 3, under the control of the controller 30. The subtraction by the subtracter 236 can extract frequency components corresponding to the thickness of the puncture needle 3 from the fundamental image data.

The user often inserts the puncture needle 3 obliquely from the surface of the subject. In this case, the weak smoothing processor 234 and the strong smoothing processor 235 use the detection area 50 in FIG. 6A, and the subtraction by the subtracter 236 allows the needle area that passes through the weak smoothing region 52A to be emphasized (to have large differences after subtraction) in the detection area 50. In specific, the puncture needle 3 inserted vertically or obliquely is emphasized in the fundamental image, whereas the puncture needle 3 inserted horizontally and tissues of the subject that extend horizontally are not emphasized in the fundamental image.

In the case of inserting the puncture needle 3 horizontally from the surface of the subject by the user, the smoothing based on the detection area 50 in FIG. 6A cannot emphasize the needle area representing the horizontally inserted puncture needle 3 in the fundamental image. Therefore, the weak smoothing processor 234 and the strong smoothing processor 235 may use the detection area 50 composed of a weak smoothing region 52B and a strong smoothing region 53B, as illustrated in FIG. 6B.

Figure 6B:
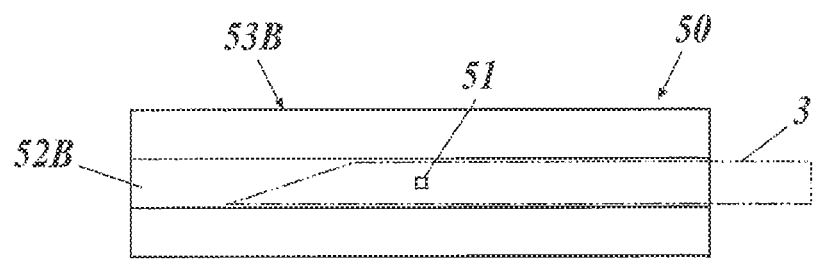
FIG. 6B illustrates a second example of smoothing regions.

The detection area 50 in FIG. 6B includes the smoothing target pixel 51 near the center, and is composed of the weak smoothing region 52B, which has a rectangular shape and occupies only the central part in the vertical direction of the detection area 50, and the strong smoothing region 53B, which has a rectangular shape and ranges over the entire detection area 50.

The weak smoothing processor 234 and the strong smoothing processor 235 use the detection area 50 in FIG. 6B, and the subtraction by the subtracter 236 allows the needle area that passes through the weak smoothing region 52B to be emphasized in the detection area 50. In specific, the puncture needle 3 inserted horizontally or obliquely is emphasized in the fundamental image. It should be noted that tissues of the subject that extend horizontally are also emphasized, whereas the puncture needle 3 inserted vertically and tissues of the subject that extend vertically are not emphasized.

Figure 6C:
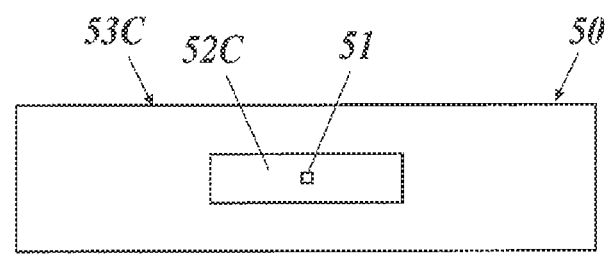
FIG. 6C illustrates a third example of smoothing regions.

Alternatively, the weak smoothing processor 234 and the strong smoothing processor 235 may use the detection area 50 composed of a weak smoothing region 52C and a strong smoothing region 53C, as illustrated in FIG. 6C.

The detection area 50 includes the smoothing target pixel 51 near the center, and is composed of the weak smoothing region 52C, which has a rectangular shape and occupies only the central part in the horizontal and vertical directions of the detection area 50, and the strong smoothing region 53C, which has a rectangular shape and ranges over the entire detection area 50.

The weak smoothing processor 234 and the strong smoothing processor 235 use the detection area 50 in FIG. 6C, and the subtraction by the subtracter 236 allows the needle area that passes through the weak smoothing region 52C to be emphasized in the detection area 50. In specific, the puncture needle 3 inserted horizontally, vertically, or obliquely is emphasized in the fundamental image. It should be noted that tissues of the subject that extend horizontally or vertically are also emphasized.

In the smoothing based on averaging, the weak smoothing processor 234 smooths a smaller region with lower intensity than the strong smoothing processor 235. In other words, the strong smoothing processor 235 smooths a larger region with higher intensity than the weak smoothing processor 234.

Alternatively, the image may be smoothed by Gaussian smoothing. In this case, a larger variance of Gaussian smoothing provides smoothing with larger intensity.

The Gaussian smoothing uses the variance in the horizontal direction among the variances in the horizontal and vertical directions.

With reference to FIG. 4, the contrast corrector 237 provides the needle image data received from the subtracter 236 with contrast between a needle area and a non-needle area through, for example, contrast correction involving gradation correction based on a sigmoid function, under the control of the controller 30.

The multiplier 238 multiplies the brightness values of the respective pixels of the needle image data after contrast correction received from the contrast corrector 237 by the synthesizing factor, which is input by the user from the input operation unit 11 via the controller 30, to generate and output the needle image data multiplied by the synthesizing factor, under the control of the controller 30.

The harmonic image generator 251 stores pieces of harmonic line data, which is received from the switch 22, into the frame memory 26, under the control of the controller 30. After storing a single frame of harmonic line data, the harmonic image generator 251 reads the single frame of harmonic line data from the frame memory 26 and outputs the single frame of harmonic image data. The frame memory 26 can store at least one frame of harmonic line data.

The contrast corrector 252 performs contrast correction for harmonic images, which involves gradation correction, to the harmonic image data received from the harmonic image generator 251, and outputs the resulting data, under the control of the controller 30. The contrast correction for harmonic images lowers the brightness values of the harmonic image or darkens the image, making the needle image (especially, the needle area) outstanding against the harmonic image.

The synthesizer 27 adds the brightness values of the respective pixels of the needle image data received from the puncture needle emphasizing signal processor 23 (multiplier 238) to the brightness values of the respective pixels of the harmonic image data received from the harmonic signal processor 25 (contrast corrector 252) to combine the image data together, and then outputs the synthesized image data, under the control of the controller 30.

The operation of the ultrasound image diagnostic apparatus U will now be explained with reference to FIG. 7. FIG. 7 illustrates example composition of ultrasound images.

The ultrasound image diagnostic apparatus U starts ultrasound image diagnosis in response to input of a display depth and a synthesizing factor by a user and appropriate inserting of the puncture needle 3 into a subject. In the ultrasound image diagnostic apparatus U, the transceiver A repeats alternating generation of driving signals corresponding to positive fundamental waves and driving signals corresponding to negative fundamental waves for each line on the basis of THI. These driving signals cause the ultrasound probe 2 to transmit and receive ultrasound waves, providing sound ray data on response signals corresponding to the ultrasound waves.

The sound ray data on the positive pulse signals from the transceiver A is directly output from the line adding unit B and is also stored into the line memory 14. The line-signal processor C converts the sound ray data on the positive pulse signals received from the line adding unit B into fundamental line data through the processes for fundamental images involving filtering, envelope detection, and log compression. The frame-signal processor D then stores the fundamental line data received from the line-signal processor C into the frame memory 24.

The line adding unit B adds the sound ray data on the negative pulse signals, which is subsequently output from the transceiver A, to the sound ray data on the positive pulse signals stored in the line memory 14, and then outputs the resulting sound ray data. The line-signal processor C converts the sound ray data, which has harmonic components, received from the line adding unit B into harmonic line data through the processes for harmonic images involving filtering, envelope detection, and log compression. The frame-signal processor D then stores the harmonic line data received from the line-signal processor C into the frame memory 26.

After storing a single frame of fundamental line data in the frame memory 24 through the repetition of the above operation, the puncture needle emphasizing signal processor 23 reads the single frame of fundamental image data, generates needle image data from the fundamental image data, and then multiplies the needle image data by the synthesizing factor. Also, after storing a single frame of harmonic line data in the frame memory 26, the harmonic signal processor 25 reads the single frame of harmonic line data and performs contrast correction for harmonic images to the read data.

The frame-signal processor D (synthesizer 27) then generates synthesized image data from the single frame of needle image data and the single frame of harmonic image data. The synthesized image is transmitted through the DSC 28, and then displayed on the display 29.

For example, with reference to FIG. 7, fundamental image data on a fundamental image 60 is read from the frame memory 24, and is converted into needle image data on a needle image 70 by the weak smoothing processor 234 and the strong smoothing processor 235, which perform smoothing based on the detection area 50, and the subtracter 236. Furthermore, harmonic image data on a harmonic image 80 is read from the frame memory 26. In the needle image 70, the needle area representing the puncture needle 3 inserted obliquely has increased brightness values for emphasis, whereas the background other than the needle area has decreased brightness values, in comparison to the fundamental image 60. The muscular tissue, which extends horizontally in the lower part of the fundamental image 60, is not emphasized in the needle image 70. The harmonic image 80 has a higher spatial resolution than the fundamental image 60.

The needle image data on the needle image 70 is multiplied by a certain synthesizing factor, and is combined with the harmonic image data on the harmonic image 80 by the synthesizer 27, yielding synthesized image data on a synthesized image 90. In the synthesized image 90, the needle area has increased brightness values for emphasis as in the needle image 70, whereas the background other than the needle area has a higher spatial resolution as in the harmonic image 80.

According to the embodiment, the ultrasound image diagnostic apparatus U, for capturing an image of the subject into which the puncture needle 3 is inserted, includes: the ultrasound probe 2 to transmit ultrasound waves to the subject in response to received pulse signals and output response signals in response to received echoes from the subject; the transmitter 12 to repeat alternating supply of positive pulse signals and negative pulse signals to the ultrasound probe 2, the negative pulse signals being generated by polarity inversion of the positive pulse signals; and the receiver 13 to receive the response signals from the ultrasound probe 2 and generate sound ray data. The ultrasound image diagnostic apparatus U includes the line memory 14 to store the first sound ray data corresponding to the positive pulse signal; the adder 15 to generate harmonic line data through addition of the stored first sound ray data and the second sound ray data corresponding to the negative pulse signal; and the line-signal processor C to generate fundamental line data from the generated first sound ray data and generate harmonic line data from the harmonic sound ray data. The ultrasound image diagnostic apparatus U includes the fundamental image generator 231 to generate fundamental image data from the generated fundamental line data; a needle image generator to generate needle image data from the generated fundamental image data, the needle image data including an emphasized needle area corresponding to the puncture needle 3; the harmonic image generator 251 to generate harmonic image data from the generated harmonic line data; the synthesizer 27 to generate synthesized image data through combining the generated needle image data and the generated harmonic image data; and the controller 30 to control the display 29 to display the generated synthesized image data.

This apparatus can provide synthesized image data on the ultrasound image that clearly captures the puncture needle in the needle area based on the needle image data, and has high spatial resolution on the basis of the harmonic image data. In addition, the apparatus can obtain a single line of line data through only two cycles of transmission of positive and negative pulse signals, preventing decrease of frame rate.

The ultrasound image diagnostic apparatus U further includes the switch 16 to output one of the generated first sound ray data and the harmonic sound ray data, which is generated through addition of the first sound ray data stored in the line memory 14 and the second sound ray data corresponding to the second pulse signals. This apparatus can switch the output between the harmonic sound ray data and the first sound ray data without delay, and requires only two cycles of transception of ultrasound waves to output the sound ray data on fundamental and harmonic components, achieving a higher frame rate than that of a traditional apparatus requiring three cycles.

The line-signal processor C generates the fundamental line data through a process for fundamental images (filtering and log compression) on the generated first sound ray data, and generates the harmonic line data through a process for harmonic images (filtering and log compression) on the harmonic sound ray data. This apparatus can generate appropriate fundamental line data after the process for fundamental images and appropriate harmonic line data after the process for harmonic images. Furthermore, the apparatus has a simplified configuration because the fundamental line data and the harmonic line data share some of their paths.

In the ultrasound image diagnostic apparatus U, the needle image generator includes: the weak smoothing processor 234 to generate first smoothed image data through smoothing of the generated fundamental image data; the strong smoothing processor 235 to generate second smoothed image data through smoothing of the fundamental image data with higher intensity than the intensity of the smoothing for the first smoothed image data; and the subtracter 236 to calculate differences of the second smoothed image data from the first smoothed image data. This apparatus can further emphasize the needle area representing the puncture needle 3 in the needle image data.

The typical traditional apparatus disclosed in Patent Literature 2 for capturing an image of a puncture needle requires the emphasis of the puncture needle that is inserted obliquely from the surface of the subject.

In order to meet this requirement, the strong smoothing processor 235 performs smoothing with higher intensity in the horizontal direction than in the vertical direction on the fundamental image data in the actual dimensions. In addition, the weak smoothing processor 234 and the strong smoothing processor 235 determine a first smoothing region for generation of the first smoothed image data and a second smoothing region for generation of the second smoothed image data. The first smoothing region is disposed in the substantial center of the second smoothing region, and the first smoothing region includes a smoothing target pixel in the substantial center. Alternatively, the first smoothing region is disposed in the substantial center of the second smoothing region in the horizontal or vertical direction of the fundamental image data. This apparatus can further emphasize the needle area representing the puncture needle 3 that is inserted at least vertically or obliquely (alternatively, horizontally or obliquely) from the surface of the subject, without emphasizing tissues that extend horizontally or vertically from the surface, in the needle image data.

The ultrasound image diagnostic apparatus U further includes the input operation unit 11 to receive input of a display depth. The weak smoothing processor 234 generates the first smoothed image data with a smaller first smoothing region as the display depth increases, and the strong smoothing processor 235 generates the second smoothed image data with a smaller second smoothing region as the display depth increases. This apparatus can maintain the appropriate size (width) of the needle area in the fundamental image without becoming narrow even when the display depth increases.

The ultrasound image diagnostic apparatus U further includes the contrast corrector 237 that performs first contrast correction involving gradation correction to the needle image data, to provide the data with contrast between the needle area and the non-needle area. The resulting needle image thus has contrast between the needle area and the non-needle area.

The ultrasound image diagnostic apparatus U further includes the contrast corrector 252 that performs second contrast correction involving gradation correction to the generated harmonic image data, to lower the brightness values of the data. The resulting harmonic image thus has decreased brightness values. The synthesizer 27 generates the synthesized image data through combining the needle image data after the first contrast correction and the harmonic image data after the second contrast correction. The resulting synthesized image thus has the needle area that is brighter for emphasis in comparison to the background other than the needle area.

The ultrasound image diagnostic apparatus U further includes: the input operation unit 11 to receive input of a synthesizing factor for the needle image data; and the multiplier 238 to multiply the brightness values of the generated needle image data by the synthesizing factor. The synthesizer 27 generates the synthesized image data through combining the needle image data multiplied by the synthesizing factor and the generated harmonic image data. The user can thus apply any synthesizing factor to the needle image relative to the harmonic image.

The above description of the embodiments is focused on a mere preferred example of the ultrasound image diagnostic apparatus according to the invention, and should not be construed to limit the invention.

For example, although the apparatus repeats alternating generation of pulse driving signals corresponding to positive fundamental waves and pulse driving signals corresponding to negative fundamental waves, which are inverted from the positive fundamental waves, and generates needle image data on the basis of the response signals associated with the pulse driving signals corresponding to positive fundamental waves in the embodiment; this configuration should not be construed to limit the invention. For example, the apparatus may repeat alternating generation of pulse driving signals corresponding to negative fundamental waves and pulse driving signals corresponding to positive fundamental waves, which are inverted from the negative fundamental waves, and generate needle image data on the basis of the response signals associated with the pulse driving signals corresponding to negative fundamental waves.

Although the puncture needle emphasizing signal processor 23 generates needle image data from the fundamental line data based on the response signals associated with the pulse signals corresponding to (positive) fundamental waves in the embodiment, this configuration should not be construed to limit the invention. For example, the harmonic image generator 251 may generate harmonic image data from the fundamental line data based on the response signals associated with the pulse signals corresponding to positive and negative fundamental waves, and store the harmonic image data into the frame memory 26. In this case, the puncture needle emphasizing signal processor 23 except for the fundamental image generator 231 may generate needle image data from the generated harmonic image data, and generate synthesized image data through combining the needle image data and the harmonic image data that is stored and subject to gradation correction by the contrast corrector 252 with any input synthesizing factor. This modification does not need the switch 22, the fundamental image generator 231, and the frame memory 24, simplifying the configuration of the ultrasound image diagnostic apparatus U. This modified apparatus uses no fundamental line data, for example, so that the line adding unit B outputs sound ray data on the harmonic components without outputting sound ray data on the pulse signals corresponding to fundamental waves, whereas the line-signal processor C performs various processes to the sound ray data on the harmonic components and outputs harmonic line data.

Figure 8:
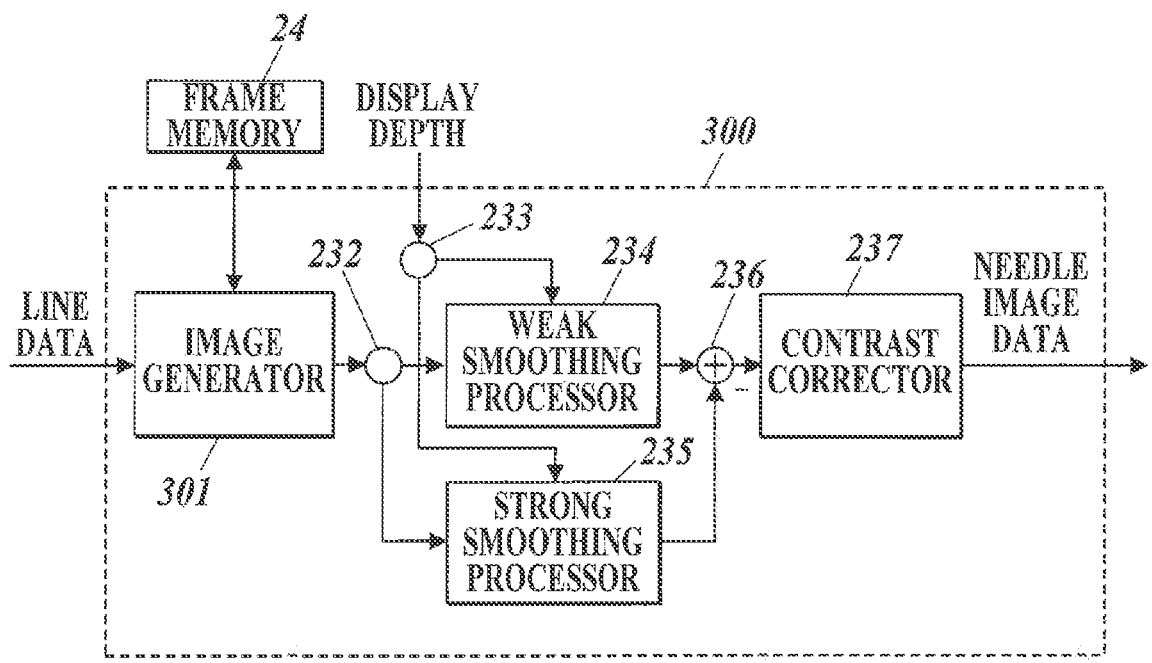
FIG. 8 is a block diagram illustrating the functional configuration of a puncture needle emphasizing signal processor according to a second embodiment.

The puncture needle emphasizing signal processor may be replaced with a puncture needle emphasizing signal processor 300 illustrated in FIG. 8. FIG. 8 is a block diagram illustrating the functional configuration of the puncture needle emphasizing signal processor 300.

With reference to FIG. 8, the puncture needle emphasizing signal processor 300 is provided with an image generator 301, in place of the fundamental image generator 231 in the puncture needle emphasizing signal processor 23 in FIG. 4. The image generator 301 receives line data on an ultrasound image from the line-signal processor.

The image generator 301 generates a single frame of image data from the received line data, and outputs emphasized needle image data, like the puncture needle emphasizing signal processor 23.

Any specific configuration or operation of each component of the ultrasound image diagnostic apparatus U in the above embodiments may be appropriately modified within the gist of the invention.

INDUSTRIAL APPLICABILITY

As described above, the ultrasound image diagnostic apparatus according to the invention can be applied to ultrasonography using a puncture needle.

REFERENCE NUMERAL LIST

U ultrasound image diagnostic apparatus
2 ultrasound probe
3 puncture needle
4 attachment
5 cable
1 ultrasound image diagnostic apparatus main unit
11 input operation unit
A transceiver
12 transmitter
121 clock generating circuit
122 pulse generating circuit
123 voltage-duty determiner
124 delay circuit
13 receiver
B line adding unit
14 line memory
15 adder
16 switch
C line-signal processor
17 dynamic filter
18 factor memory
19 detecting processor
20 log compressing processor
21 factor memory
D frame-signal processor
22 switch
23, 300 puncture needle emphasizing signal processor
231 fundamental image generator
232, 233 branch
234 weak smoothing processor
235 strong smoothing processor
236 subtracter
237 contrast corrector
238 multiplier
301 image generator
24, 26 frame memory
25 harmonic signal processor
251 harmonic image generator
252 contrast corrector
27 synthesizer
28 DSC
29 display
30 controller

The invention claimed is:

1. An ultrasound image diagnostic apparatus for capturing an image of a subject into which a puncture needle is inserted, the apparatus comprising:
    an ultrasound probe to transmit ultrasound waves to the subject in response to received pulse signals and output response signals in response to received echoes from the subject;
    a transmitter to repeat alternating supply of first pulse signals and second pulse signals to the ultrasound probe, the second pulse signals being generated by polarity inversion of the first pulse signals;
    a receiver to receive the response signals from the ultrasound probe and generate first sound ray data corresponding to the first pulse signals and second sound ray data corresponding to the second pulse signals;
    a line-signal processor,
    a harmonic sound ray data generator receiving the first sound ray data and the second sound ray data from the receiver, the harmonic sound ray data generator including a line memory, the harmonic sound ray data generator storing the first sound ray data corresponding to the first pulse signals in the line memory and outputting the first sound ray data to the line-signal processor when the first sound ray data is received from the receiver, and the harmonic sound ray data generator including an adder generating harmonic sound ray data based on the stored first sound ray data and the second sound ray data corresponding to the second pulse signals and outputting the generated harmonic sound ray data to the line-signal processor when the second sound ray data is received from the receiver, the harmonic sound ray data generator including a switch switchable between a first position at which a path to the receiver is connected to the line-signal processor and a path to the adder is not connected to the line-signal processor and a second position at which the path to the adder is connected to the line-signal processor and the path to the receiver is not connected to the line-signal processor,
    wherein the line-signal processor generates fundamental line data from the generated first sound ray data and generates harmonic line data from the generated harmonic sound ray data;
    a fundamental image generator to generate fundamental image data from the generated fundamental line data;
    a needle image generator to generate needle image data by processing the generated fundamental image data, the generated needle image data including an emphasized needle area corresponding to the puncture needle;
    a harmonic image generator to generate harmonic image data from the generated harmonic line data;
    a synthesizer to generate synthesized image data through combining the generated needle image data and the generated harmonic image data; and
    a display controller to control a display to display the generated synthesized image data.

2. The ultrasound image diagnostic apparatus according to claim 1, wherein the line-signal processor generates the fundamental line data through a process for fundamental images on the generated first sound ray data, and generates the harmonic line data through a process for harmonic images on the generated harmonic sound ray data.

3. The ultrasound image diagnostic apparatus according to claim 1, wherein the needle image generator comprises:
   a first smoothing processor to generate first smoothed image data through a first smoothing of the generated fundamental image data,
      wherein the first smoothing is performed with a first intensity;
   a second smoothing processor to generate second smoothed image data through a second smoothing of the generated fundamental image data,
      wherein the second smoothing is performed with a second intensity, and the second intensity is higher than the first intensity; and
   a subtracter to calculate differences of the second smoothed image data from the first smoothed image data.

4. The ultrasound image diagnostic apparatus according to claim 3, wherein the second smoothing processor performs smoothing with higher intensity in a horizontal direction than in a vertical direction on the generated fundamental image data in the actual dimensions.

5. The ultrasound image diagnostic apparatus according to claim 3, wherein the needle image generator determines a first smoothing region for generation of the first smoothed image data and a second smoothing region for generation of the second smoothed image data, the first smoothing region being disposed in the center of the second smoothing region, the first smoothing region including a smoothing target pixel in the center of the first smoothing region.

6. The ultrasound image diagnostic apparatus according to claim 5, wherein the first smoothing region is disposed in the center of the second smoothing region in the horizontal or vertical direction of the generated fundamental image data.

7. The ultrasound image diagnostic apparatus according to claim 5, further comprising a first input unit to receive input of a display depth, wherein the first smoothing processor generates the first smoothed image data with a smaller first smoothing region as the display depth increases, and the second smoothing processor generates the second smoothed image data with a smaller second smoothing region as the display depth increases.

8. The ultrasound image diagnostic apparatus according to claim 1, further comprising a first contrast corrector to perform first contrast correction involving gradation correction to the generated needle image data.

9. The ultrasound image diagnostic apparatus according to claim 1, further comprising a second contrast corrector to perform second contrast correction involving gradation correction to the generated harmonic image data.

10. The ultrasound image diagnostic apparatus according to claim 1, further comprising: a second input unit to receive input of a synthesizing factor for the generated needle image data; and a multiplier to multiply brightness values of the generated needle image data by the input synthesizing factor, wherein the synthesizer generates the synthesized image data through combining the generated needle image data multiplied by the synthesizing factor and the generated harmonic image data.

11. The ultrasound image diagnostic apparatus according to claim 1, wherein the needle image generator infers a background of an input image and extracts the difference between the background and the input image to emphasize the needle area corresponding to the puncture needle.

12. The ultrasound image diagnostic apparatus according to claim 1, wherein the line-signal processor requires only two cycles of transception of ultrasound waves based on the first pulse signals and the second pulse signals to generate the fundamental line data and the harmonic line data.

13. The ultrasound image diagnostic apparatus according to claim 1, wherein the switch is switched to the first position when the first sound ray data is received from the receiver and is switched to the second position when the second sound ray data is received from the receiver.

* * * * *